United States Patent
Tu et al.

(10) Patent No.: US 6,283,962 B1
(45) Date of Patent: Sep. 4, 2001

(54) DEVICE FOR VALVULAR ANNULUS TREATMENT AND METHODS THEREOF

(75) Inventors: Hosheng Tu; Steve Chun-Guang Tu, both of Tustin, CA (US)

(73) Assignee: Quantum Therapeutics Corp., Dana Point, CA (US)

(*) Notice: Subject to any disclaimer, the term of this patent is extended or adjusted under 35 U.S.C. 154(b) by 0 days.

(21) Appl. No.: 09/456,769

(22) Filed: Dec. 7, 1999

Related U.S. Application Data (63) Continuation-in-part of application No. 09/093,586, filed on Jun. 8, 1998, now Pat. No. 5,997,534.

(51) Int. Cl.$^7$ .................................................. A61B 18/18
(52) U.S. Cl. ............................... 606/41; 606/47; 606/49; 607/102; 128/898
(58) Field of Search ......................... 606/41–50, 170, 606/171, 180; 607/101, 102, 119, 122

(56) References Cited

U.S. PATENT DOCUMENTS

| | | | |
|---|---|---|---|
| 5,527,331 | * 6/1996 | Kresch et al. ................... 606/170 |
| 5,728,143 | * 3/1998 | Gough et al. .................... 607/101 |
| 5,733,277 | * 3/1998 | Pallarito ................................ 606/7 |
| 5,769,880 | * 6/1998 | Truckai et al. .................. 607/101 |
| 5,810,804 | * 9/1998 | Gough et al. ..................... 606/41 |
| 5,904,681 | * 5/1999 | West, Jr. ............................ 606/41 |
| 6,039,748 | * 3/2000 | Savage et al. ................... 606/180 |
| 6,076,012 | * 6/2000 | Swanson et al. ................. 604/21 |
| 6,105,581 | * 8/2000 | Eggers et al. .................. 128/898 |
| 6,113,594 | * 9/2000 | Savage ................................ 606/41 |
| 6,179,832 | * 1/2001 | Jones et al. ....................... 606/32 |

\* cited by examiner

*Primary Examiner*—John P. Leubecker
*Assistant Examiner*—David M. Ruddy (57) ABSTRACT

A medical ablation device system for treating endometrosis, gingivae, valvular annulus, or reducing the mass of cellular tissues, wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues.

17 Claims, 12 Drawing Sheets

DEVICE FOR VALVULAR ANNULUS TREATMENT AND METHODS THEREOF

CROSS-REFERENCE TO RELATED APPLICATIONS

This patent application is a continuation-in-part application of application Ser. No. 09/093,586, entitled "Medical Ablation Device System and Methods Thereof" filed Jun. 8, 1998, now U.S. Pat. No. 5,997,534, issued on Dec. 7, 1999, and is incorporated herein by reference.

FIELD OF THE INVENTION

The present invention generally relates to an improved device and methods for medical purposes, and more particularly, to such a device and methods for providing appropriate heat treatment in a patient by delivering thermal energy to an endometrosis site, valvular annulus, or other tissues, and a simultaneously continuous sweeping massage therapy.

BACKGROUND OF THE INVENTION

Endometrosis is a condition in which fragments of the lining of the uterus spread to other tissues, such as the wall of the uterus, the ovaries, the peritoneum, or the bowel. The causes of the disease are unknown, but its incidence is higher in women who defer pregnancy. The fragments are benign, but may cause complications if they lodge in a critical location, leading to an organ dysfunction.

There are no definite symptoms of endometrosis, and the condition is found only during a surgical operation for other disorders. When endometrosis is present, symptoms include heavy periods, often more frequent than usual, accompanied by pain (dysmenorrhea); pain during sexual intercourse (dyspareunia); sometimes infertility; and sometimes pain on defecation during a period. The abnormally placed fragments of endometrium pass through the same monthly cycle, as does the normal endometrium. They swell before a period and then bleed. Because there is no outlet for the blood, cysts form. These cysts occasionally rupture, causing severe abdominal pain.

In milder cases, painkilling drugs may lesson the symptoms. However, in severe cases, surgery or laser treatment are currently the only two options. As one of the severe cases, cul-de-sac obliteration implies the presence of retrocervical deep fibrotic endometrosis. The deep fibrotic endometrosis is usually located on the upper vagina, on the superficial anterior rectum, in the rectovaginal space, in the space between the upper vagina and the cervix (cervicovaginal angle), or in one or both uterosacral ligaments. With deep cul-de-sac obliteration, fibrotic endometrosis or adhesions sometimes involve the entire area between the cervicovaginal junction and the rectovaginal septum.

Surgery exposes a patient to greater risks, due to infection and other health reasons. The laser culdotomy, a procedure for the removal of cul-de-sac obliteration, poses a risk of unwanted tissue perforation or tissue vaporization. A less invasive approach using RF therapeutic protocols, has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, when coupled with a temperature control mechanism, can supply precise energy to the device-to-tissue contact site to obtain the desired thermal energy for treatment.

To be more efficient in RF energy ablations, the electrode with a rotational sweeping capability to cover the broad area is used to simultaneously deliver the sweeping massage therapy to the target tissue. Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula, and RF energy is applied to the uvula tissue to cause internal lesions. However, Edwards et al. does not disclose a device to ablate tissues, in which there is the capability for simultaneously delivering radiofrequency energy and rotational sweeping massage therapy.

The human's circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole. The pulmonary valve separates the right ventricle from the pulmonary artery. The mitral valve, so named because of its resemblance to a bishop's mitre, is in the left ventricle and it separates the left atrium from the ventricle. The fourth valve is the aortic valve that separates the left ventricle from the aorta. In a venous circulatory system, a venous valve is to prevent the venous blood from leaking back into the upstream side so that the venous blood can return to the heart and the lungs for blood oxygenating purposes.

In either the case of valvuloplasty or valvular dysfunction, the annular organ structure of a heart valve, a valve leaflet, a chordae tendinae, papillary muscles, a venous valve, and the like still needs to be treated and/or tightened so that the valvular function is competent. The current technology for valve repair or valve replacement requires an expensive open-heart surgery that needs a prolonged period of recovery. A less invasive catheter-based valve repair technology having capability for simultaneously delivering radiofrequency energy and rotational sweeping massage therapy becomes an unmet clinical challenge.

Therefore, there is a clinical need to have a less invasive catheter-based approach for treating the endometrosis, an annular organ structure of a heart valve, a venous valve, a valve leaflet, a chordae tendinae, papillary muscles, tumors, and the like by using high frequency energy with rotational sweeping massage therapy for reducing and/or shrinking a tissue mass for tightening and stabilizing the dilated tissue adjacent a valvular annulus or an annular organ structure.

SUMMARY OF THE INVENTION

In general, it is an object of the present invention to provide a method and an improved medical ablation device or a catheter for generating heat, to treat endometrosis, cysts, polyps, prostate, tumors, valvular annulus, or cellular tissues. It is another object of the present invention to provide a device in which rotational sweeping massage therapy is applied to the endometrosis, cysts, polyps, prostate, tumors, valvular annulus, or the target cellular tissues, for intimate contact. The "rotational sweeping massage" in this invention implies that the surface of a rotational device (e.g., a plate-like electrode or a cam-type electrode) continuously or intermittently contacts a target tissue with a normal sweeping force by the rotational device. The "target tissue" in this invention indicates the endometrosis, the cysts, the gingivae, the tumor, the prostate, the polyp, the valvular annulus, or other cellular tissues.

It is another object of the present invention to provide a method and a device for monitoring the temperature of the medical device, and to control the temperature by utilizing a temperature control mechanism and/or algorithm. The location of the temperature sensor is preferably at the proximity of the tip portion of the medical device. It is still another object of this invention to provide methods and a device for treating the endometrosis, cysts, polyps, prostate, tumors, valvular annulus, or cellular tissues in a patient by delivering a therapeutic agent to the target site.

Briefly, heat is generated by applying a suitable energy source to a device, including a flexible catheter-type device, which comprises an electrode, in contact with the body tissue. A suitable energy source may consist of radiofrequency energy, microwave energy, ultrasonic energy, alternating current energy, or laser energy. The energy is applied to the endometrosis, cysts, canker sore, gingivae, polyps, tumors, prostate, valvular annulus, or other cellular tissues through the electrode. A DIP (dispersive indifferent pad) type electrode, that contacts the patient, is connected to the Indifferent Electrode Connector on the RF generator. When using an alternating current electrical outlet, the generator should be grounded to avoid electrical interference. Heat is controlled by the power of the RF energy being delivered, by the delivery duration, and by the delivery mode. The standard RF energy generator principles, and its applications through the electrode to a patient, are well known for those who are skilled in the art.

In a further embodiment, means for generating rotational motion for the distal section of the elongate tubular element of the catheter system comprises a motor mounted in a cavity of the handle, which has a rotatable motor shaft, an elongate connecting shaft having a first end to which the proximal end of the elongate tubular element is connected, and a second end connected to the motor, so that when the motor shaft rotates, the elongate tubular element also rotates.

In one embodiment, the device is leak-proof so that the therapeutic agent, in either fluid phase or gel phase, is forced under a positive pressure to flow inside the lumen of the medical device from its proximal end to the distal end. The fluid is vented through an opening at the proximity of the electrode to effect the therapeutic purposes to the target tissue site.

The methods and device of the present invention have several significant advantages over other known systems or techniques to treat the endometrosis, the cysts, the canker sore, the gingivae, the polyps, the prostate, the tumors, the valvular annulus, or other cellular tissues. In particular, the device system comprising the electrode, using RF energy as a heat source, in this invention, and simultaneously delivering rotational sweeping massage therapy to the target tissue sites, results in a more efficient therapeutic effect, which is highly desirable in its intended application on treating the endometrosis, cysts, canker sores, gingivae, polyps, tumors, prostate, valvular annulus, other cellular tissues, or other medical applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIG. 4-A is a perspective view of the electrode, which is a pre-shaped curved plate.

FIG. 4-B is a perspective view of the electrode, which includes a plurality of pre-shaped curved wires.

FIG. 4-C is a perspective view of the electrode, which is a pre-shaped curved mesh.

DETAILED DESCRIPTION OF EXEMPLARY EMBODIMENTS

Figure 1:
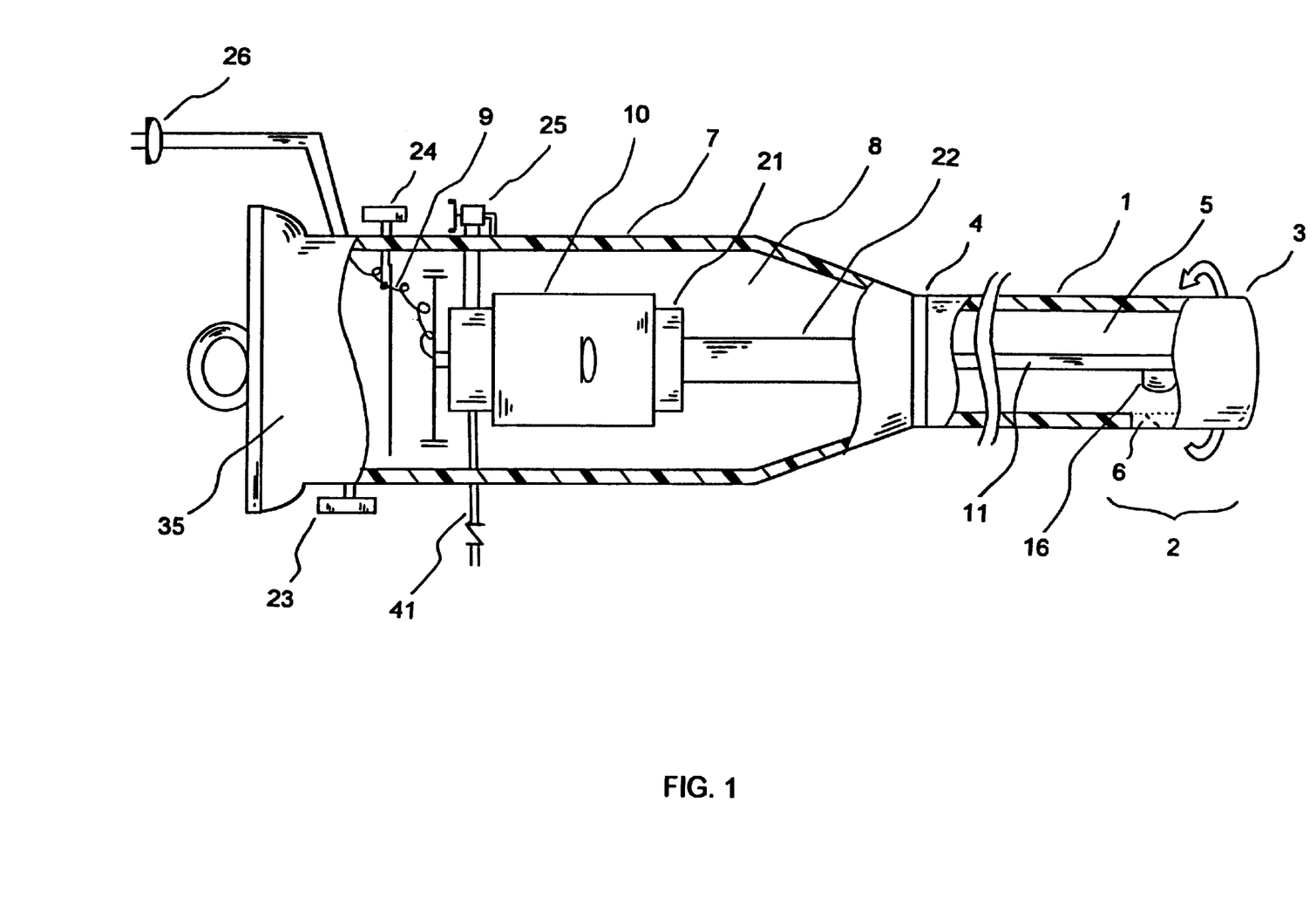
FIG. 1 is an overall view of the medical device, having an electrode with heat generating source and a rotation generating means for generating rotation of the tip portion, constructed in accordance with the principles of the present invention.

Referring to FIGS. 1 to 10, what is shown is an embodiment of a medical ablation device system, comprising simultaneously applying radiofrequency energy and applying a rotational sweeping therapeutic massage to treat the endometrosis, cysts, gingivae, tumors, prostate, polyps, valvular annulus, or cellular tissues of a patient. As shown in FIG. 1, a medical ablation device system, including a flexible catheter-type device system, comprises an elongate tubular element 1 having a distal section 2, a distal end 3, a proximal end 4, and at least one lumen 5 extending between the distal end and the proximal end, wherein an opening 6 is located at one side of the distal section 2.

An inner tubing 11 is located within the lumen 5 of the elongate tubular element 1. The inner tubing 11 has a distal section 12, a distal end 13, a proximal end 14, and a lumen 15 extending between the distal end and the proximal end, wherein a deployable electrode 16 is located at the distal section 12 of the inner tubing 11. The deployable electrode 16 comprises a pre-shaped extendible electrode 17 that stays within the lumen of the elongate tubular element 1 under a non-deployed state and extends out of the elongate tubular element 1 through the opening 6 during a deployed state.

A handle 7 is attachably secured at the proximal end 4 of the tubular element 1. The handle 7 has a cavity 8. An external RF energy generator (not shown) has a conducting wire 9, wherein the RF energy is supplied to the deployable electrode 16 through the conducting wire 9. The RF energy supply is controlled by an on-off switch button 24 located conveniently on the handle 7.

The medical ablation device system, including a catheter-type device system, further comprises means for generating rotational motion for the distal section of the elongate tubular element 1. The means comprises a motor 10 mounted in the cavity 8 of the handle 7, which has a rotatable motor shaft 21 connected to an elongate connecting shaft 22 having a first end to which the proximal end 4 of the elongate tubular element 1 is coupled and connected, and a second end connected to the motor 10, so that when the motor shaft 21 rotates, the elongate tubular element 1 also rotates. The handle 7 is also equipped with an on-off electrical controller 23 for the motor 10, an on-off controller 24 for the RF energy delivery conducting wire 9, a connector 26, and an engagement controller 25, which is used to control the extending degree of the extendible electrode 17, either inside the elongate tubular element 1 or out of the opening 6 of the elongate tubular element 1.

In one embodiment, a battery means 35, which is located at the proximal end of the cavity 8 of the handle 7, is used to supply the energy to the motor 10. In an alternate embodiment, the motor 10 is powered by an alternating current (AC) through a power input plug (not shown). In either case, the power supply is controlled by an on-off switch button 23 located conveniently at the proximal end of the handle 7.

Figure 2:
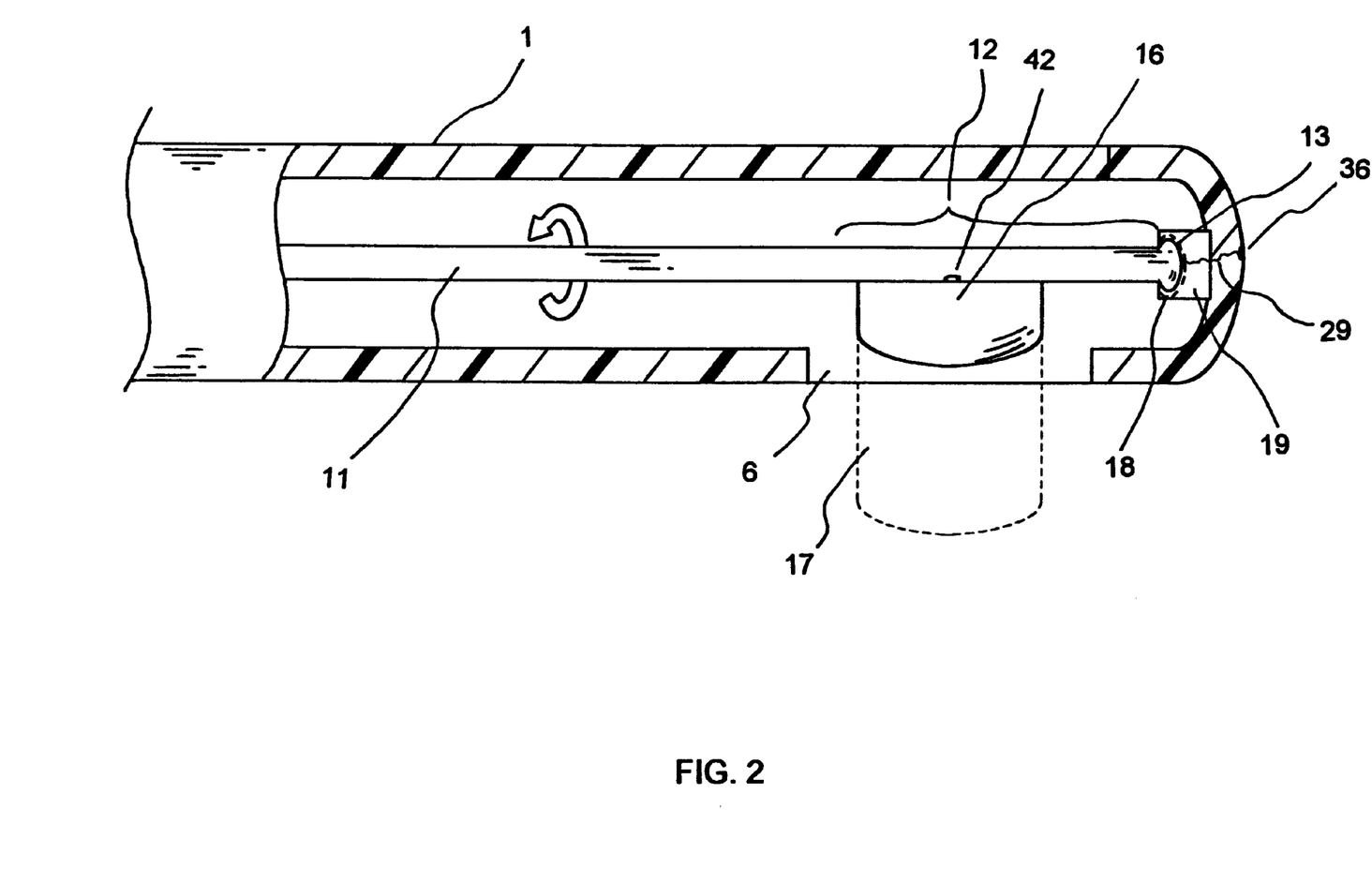
FIG. 2 is a cross-sectional view of the distal portion of the medical device in FIG. 1.

FIG. 2 shows a cross-sectional view of the distal portion of the medical device in FIG. 1. The inner tubing 11 has a deployable electrode 16 comprising a pre-shaped extendible electrode 17, and a distal end 13, wherein the distal end 13 is securely suspended inside a cavity 18 of an attachment member 19. The attachment member 19 is secured to the inner side of the distal end 3 of the elongate tubular element 1. The inner tubing 11 is rotatable relative to the elongate tubular element 1 in either direction, of which direction dictates the deployment and un-deployment states of the extendible electrode 17 from the deployable electrode 16. After deployment of the extendible electrode, the inner tubing 11 and the elongate tubular element 1 are locked together as one unit and adapted to be rotatable by the movement of the motor shaft 21.

In one preferred embodiment, the very distal end 3 of the elongate tubular element 1 is shaped as a needle so that the distal end can be inserted into the tissue to stabilize the medical ablation device system for ablative operations.

Figure 3:
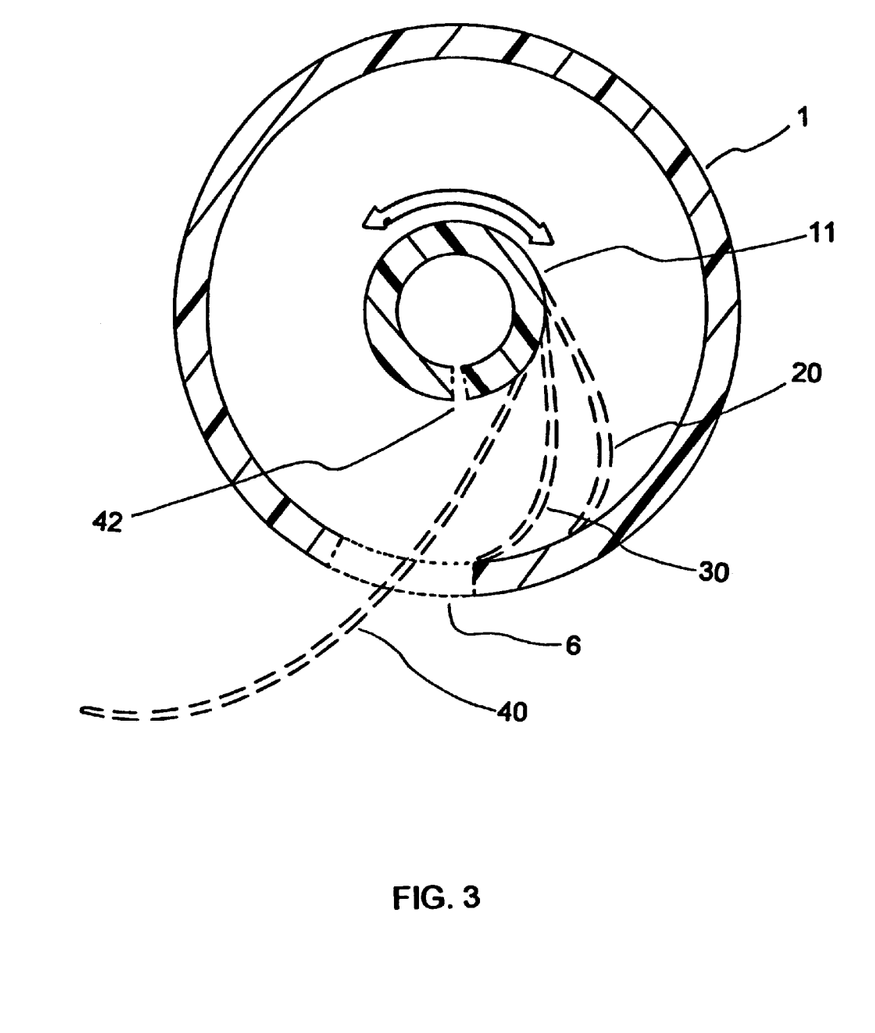
FIG. 3 is a transverse view of the electrode, including an extendible electrode.

The window dimensions of the opening 6 of the elongate tubular element 1 are such that the extendible electrode 17 is free to deploy and retract without undue obstruction. FIG. 3 shows a transverse view of the electrode 16, including an extendible electrode 17. The extendible electrode 17 can be adjusted in several different deployment states, such as the non-deploy state 20, the ready-to-deploy state 30, and fully deployed state 40.

Figure 4:
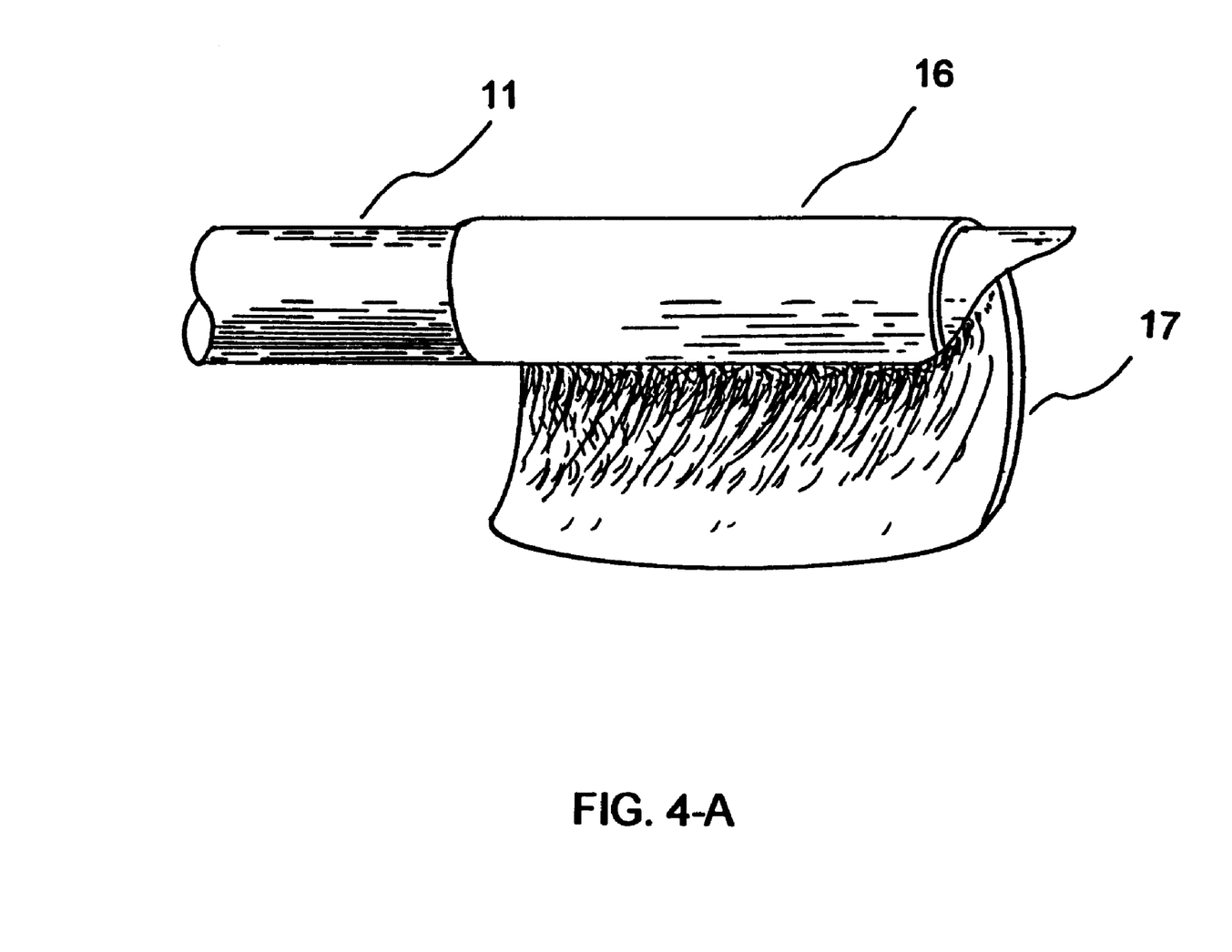

FIG. 4-A to FIG. 4-C show some of the perspective views of the deployable electrode. The extendible electrode 17 may be selected from the group consisting of a curved plate, a plurality of curved wires, a curved plate with studded surface, a plurality of coils, a meshed plate, a curved wire with a needle end, and the like. Because of its pre-shaped memory and material strength, the curved electrode 17 is advanced out of the opening 6 during the deployment phase. As shown in FIG. 3, the elongate tubular element 1 may be rotated in the same direction as the extendible electrode; in this case, the counter-clockwise direction to effect the rotational sweeping massage therapy to the target tissue. However, for the extendible electrode 17 to penetrate into a tissue for cell necrosis purposes, the elongate tubular element 1 may be rotated in the opposite direction as the extendible electrode 17.

Figure 5:
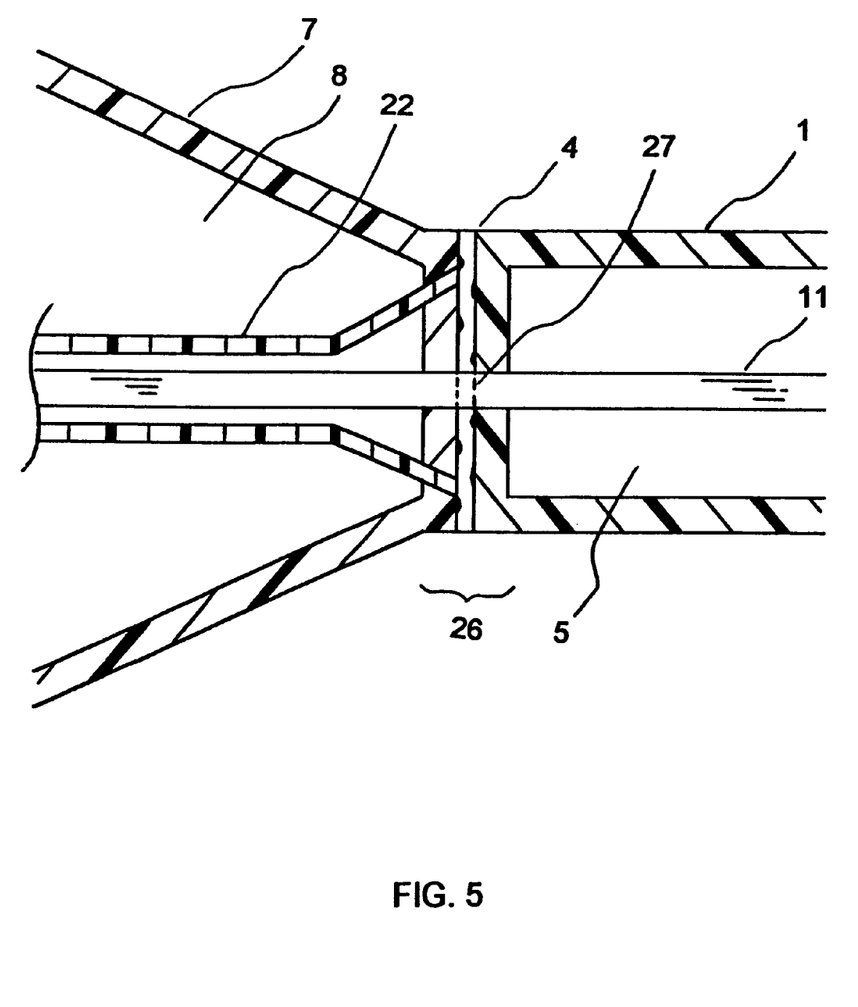
FIG. 5 is a cross-sectional view of a coupling mechanism between an elongate tubular element of the medical device and a handle portion.

FIG. 5 shows a cross-sectional view of the coupling mechanism between an elongate tubular element 1 of the medical device and a handle portion 7. The coupling mechanism 26 comprises two members: the distal tubular portion and the proximal handle portion of the medical ablation device system. The proximal handle portion of the coupling mechanism 26 is secured to the elongate connecting shaft 22, wherein the elongate connecting shaft is connected to the motor shaft 21. The distal tubular portion includes a proximal end 4 of the tubular element 1, a first transitional end 27 of the inner tubing 11, a first conducting wire 28 for the RF energy delivery, a first temperature sensing wire 29 for the optional temperature sensors, and a locking groove 31 with a plurality of locking elements 32. The proximal handle portion includes their corresponding matching ends on the other member of the coupling mechanism.

Figure 6:
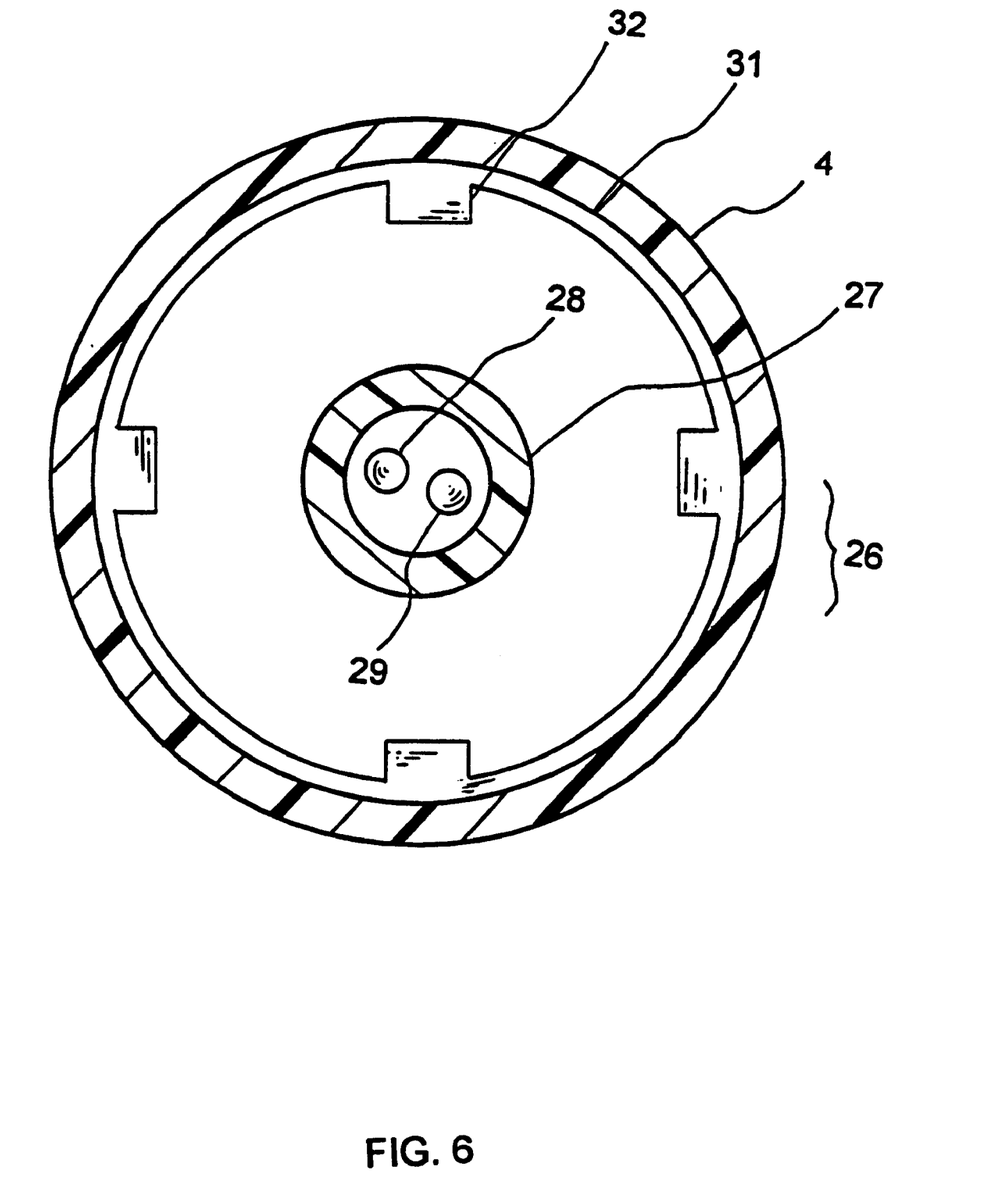
FIG. 6 is a transverse view of the coupling mechanism of FIG. 4.

FIG. 6 shows a transverse view of the coupling mechanism of FIG. 5. When coupled, the distal tubular portion of the device and the proximal portion (i.e., the handle) of the device become one unit. The distal tubular portion is thereafter rotatable with respective to the handle portion. When uncoupled, the first transitional end 27 of the inner tubing 11 and its counterpart of a second transitional end (not shown) of the proximal portion of the inner tubing, that is located inside the cavity 8 of the handle 7, is temporarily dissociated from the coupling mechanism 26. During the uncoupled phase, the inner tubing is free to rotate so that the extendible electrode 17 can be deployed or retracted.

Figure 7:
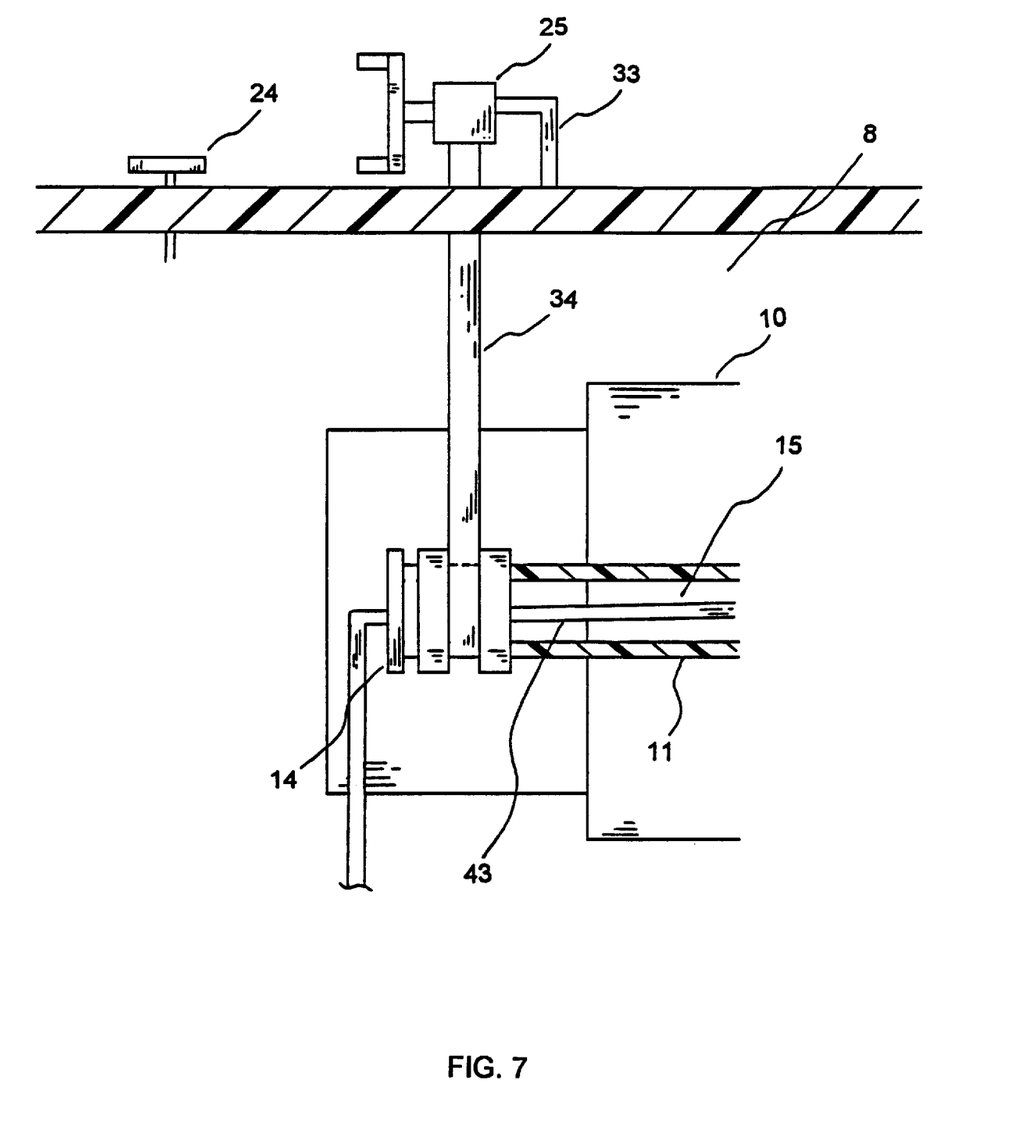
FIG. 7 is a cross-sectional view of a control mechanism of the inner tubing at its proximal portion.

FIG. 7 shows a cross-sectional view of a control mechanism of the inner tubing at its proximal portion. The proximal end 14 of the inner tubing 11 extends all the way to the handle portion. A conveying means 34, either a belt-type or chain-type, is used to connect the proximal portion 14 of the inner tubing 11 to an external controller 25. The engagement controller 25 is used to advance the extendible electrode 17 out of the opening 6 of the elongate tubular element 1 and/or retract it back to inside the lumen 5 of the tubular element 1. The engagement controller 25 is equipped with a level adjuster 33 so that the controller 25 is functional only when the coupling mechanism 26 is in the uncoupled state. In other words, the level adjuster 33 makes the engagement controller 25 non-functional when the coupling mechanism 26 is in the coupled state.

The extendible electrode 17 is preferably selected from the group consisting of platinum, iridium, gold, silver, stainless steel, Nitinol, tungsten, and an alloy of their mixtures. The outer surface of the medical device, except the electrode at its distal portion, is not conductive. A conducting wire 9 is used to transmit the RF energy from the external RF generator to the deployable electrode 16. One end of the conducting wire 9 is secured and connected to the electrode 16 at the distal section 2 while the other end of the conducting wire 9 is secured to a contact pin of the connector 26, wherefrom the conducting wire 9 is connected to an external RF generator (not shown) or other energy source.

In one embodiment, a temperature sensor 36 is disposed close to the electrode 16. An insulated temperature sensor wire 29 passes from the temperature sensor 36 at the distal end, through the lumen 15 of the inner tubing 11, to an external temperature controller through the outlet connector 26. The energy delivery is controlled by the measured temperature from the temperature sensor 36, a closed-loop temperature control mechanism and/or an algorithm. When the measured temperature rises to the preset high-limit point, the temperature control mechanism sends out a signal to cut off the energy supply. In a similar manner, when the measured temperature drops to the preset low-limit point, the temperature control mechanism sends out a signal to activate the energy supply. The control mechanism can be a proportional mode, a derivative mode, an integral mode, or a combination of the above modes. The RF energy delivery can also be operated in a Power Control Mode, which is not controlled by any temperature factor.

In another embodiment, a fluid infusion means 41 for infusing fluid to the device is provided for the irrigation of a desired therapeutic agent, in either fluid phase or gel phase, to the endometrosis site, to the valvular annulus site, or to other target cellular tissue site. The fluid is adapted to diffuse out of the inner tubing 11 at an inner opening 42 at the proximity of the electrode 16. The therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics and/or their mixtures. A passage 43 is provided inside the lumen of the inner tubing 11 for transporting the fluid or gel from the proximal end 14 of the inner tubing 11 to the distal end 13. Thereafter the fluid or gel is diffused out of the inner tubing 11 through the inner opening 42 and thereafter out of the tubular element 1 through the opening 6.

Figure 8:
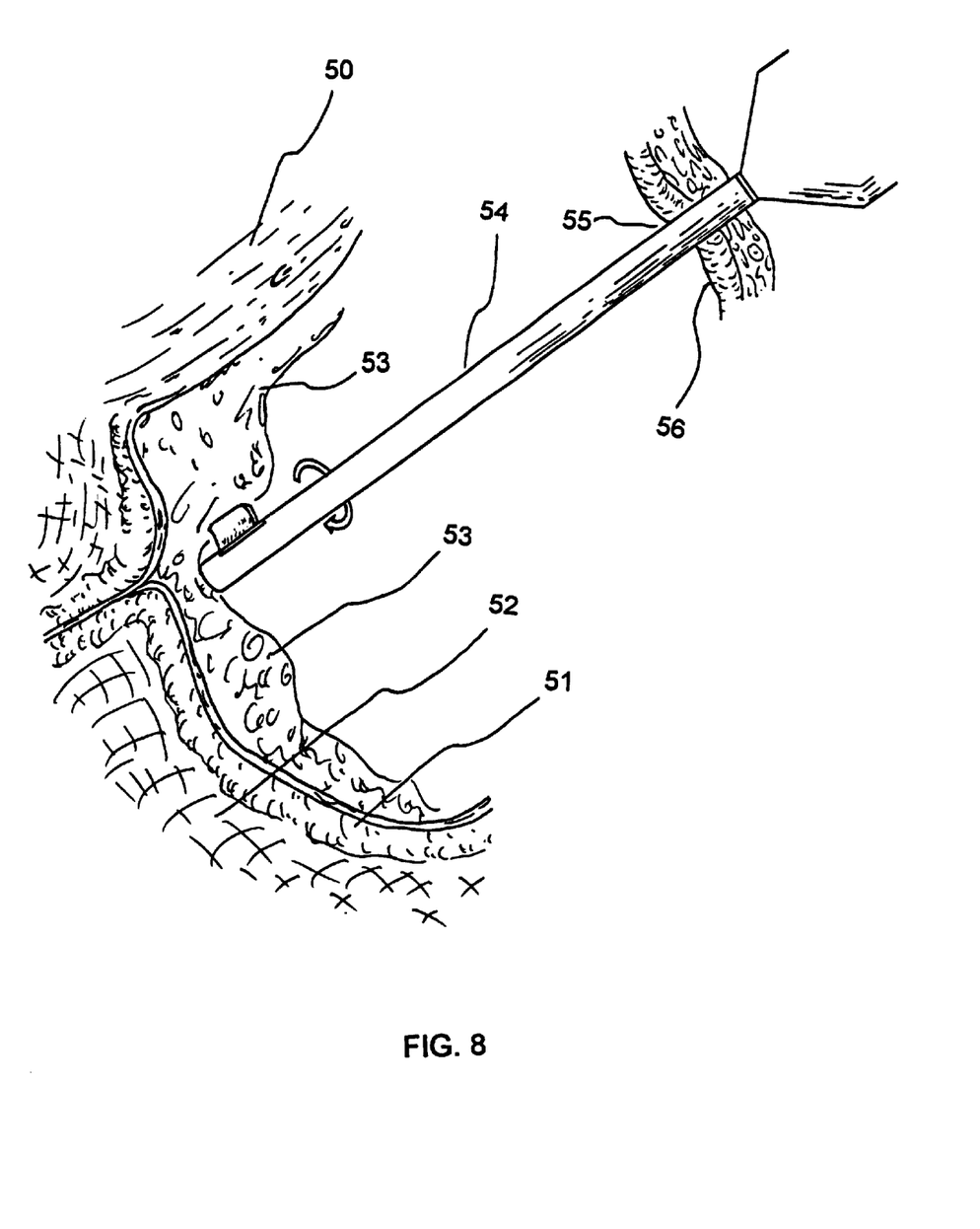
FIG. 8 is a simulated perspective view of the endometrosis being treated by the medical device of the present invention.

FIG. 8 shows a simulated perspective view of the endometrosis being treated by the medical ablation device of the present invention. For illustration purposes, the uterus 50 of a patient is briefly shown here. The rectum 51 and the rectal wall 52 are at the lower part of FIG. 8, wherein the endometrosis 53 is shown at the exterior wall of the uterus 50. A medical ablation device 54 of the present invention is inserted through the puncture 55 of the skin 56, following a standard laparoscopic approach. To position the patient for a more effective ablation, the uterus may be optionally stretched anteriorly using a uterine elevator, while the rectum is retracted from the uterus and vagina by a rectal probe.

The distal end of the ablation device 54 is positioned against the wall of the rectum and uterine. Thereafter, the extendible electrode 17 is advanced out of the elongate tubular element 1 and the coupling mechanism 26 is activated. The device is now ready for RF energy ablation in association with the rotational sweeping massage therapy. Optionally, the fluid can be infused to effect the cooling of the electrode and for the therapeutic purposes. In one embodiment, the external RF energy generator has the capability to supply RF energy by controlling the time, power, and temperature through an optional separate closed-loop temperature control means. The patient is connected to the RF generator through a DIP electrode to form a closed-loop current system. Therefore, RF energy is applied and delivered to the target endometrosis site, through the electrode 17 of this invention.

The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and applying the rotational sweeping massage therapy topically, the endometrosis disease or abnormal valvular annulus can be treated.

A method for treating the endometrosis of a patient with a medical ablation device system comprises: inserting the medical ablation device system into the abdominal cavity of a patient using a standard laparoscopic technique; positioning the tip of the device system upon the wall of the abdominal cavity where an endometrosis prevails, deploying the extendible electrode out of the opening of the elongate tubular element of the device system; applying RF energy to the extendible electrode of the device system to effect heat treatment of the endometrosis.

In an alternate embodiment, the method for treating the endometrosis of a patient with a medical ablation device system comprises: inserting the medical ablation device system into the uterus of a patient using a standard inserting technique; positioning the tip of the device system upon the wall of the uterus where an endometrosis prevails, deploying the extendible electrode out of the opening of the elongate tubular element of the device system; applying RF energy to the extendible electrode of the device system to effect heat treatment of the endometrosis.

Figure 9:
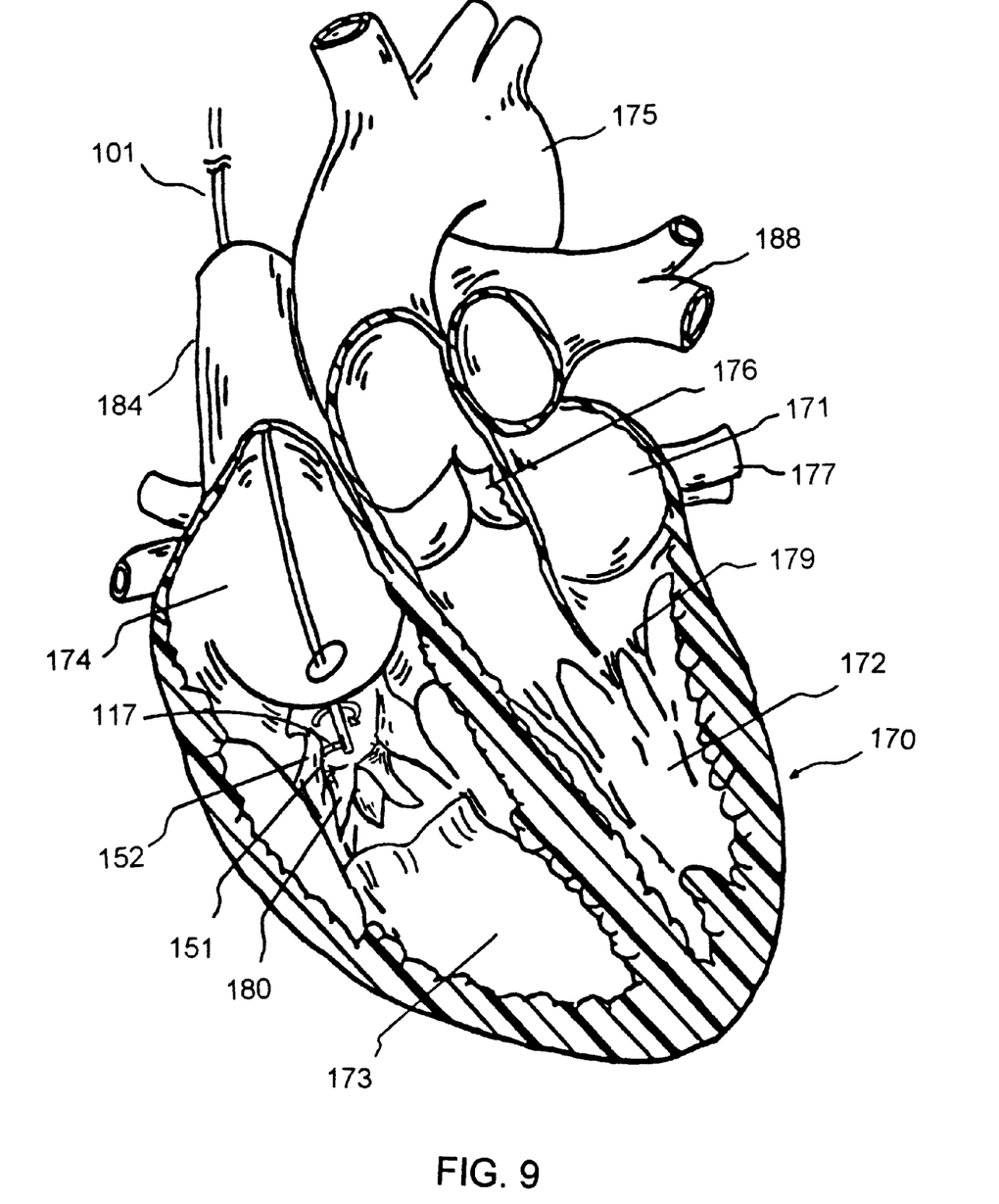
FIG. 9 is a simulated perspective view of the valvular annulus being treated by the medical catheter of the present invention.

In another tissue treatment application, FIG. 9 shows a simulated perspective view of a valvular annulus being treated by the medical catheter of the present invention. For illustration purposes, the heart 170 has a left atrium 171, a left ventricle 172, a right ventricle 173, and a right atrium 174. Aorta 175 connects with the left ventricle 172 and contains an aorta valve 176. Pulmonary artery 177 connects with the right ventricle 173 through a pulmonary valve. Left atrium 171 communicates with the left ventricle 172 through a mitral valve 179. The right atrium 174 communicates with the right ventricle 173 through a tricuspid valve 180. Oxygenated blood is returned to the heat 170 via pulmonary veins 188. In a perspective illustration, a catheter 101 is inserted into the right atrium 174 and is positioned on the inner wall 151 of the tricuspid valve 180. The leaflets of the tricuspid valve 180 open toward the ventricle side. Blood returned from the superior vena cava 184 and the inferior vena cava flows into the right atrium 174. Subsequently, blood flows from the right atrium 174 to the right ventricle 173 through the tricuspid valve 180. The extendible electrode 117 is to contact the tissue of an annular organ structure 152. Therefore, the extendible electrode 117 when deployed from the catheter shaft from the atrial side does not interfere with the leaflet movement during the proposed minimum invasive thermal therapy of the invention.

Figure 10:
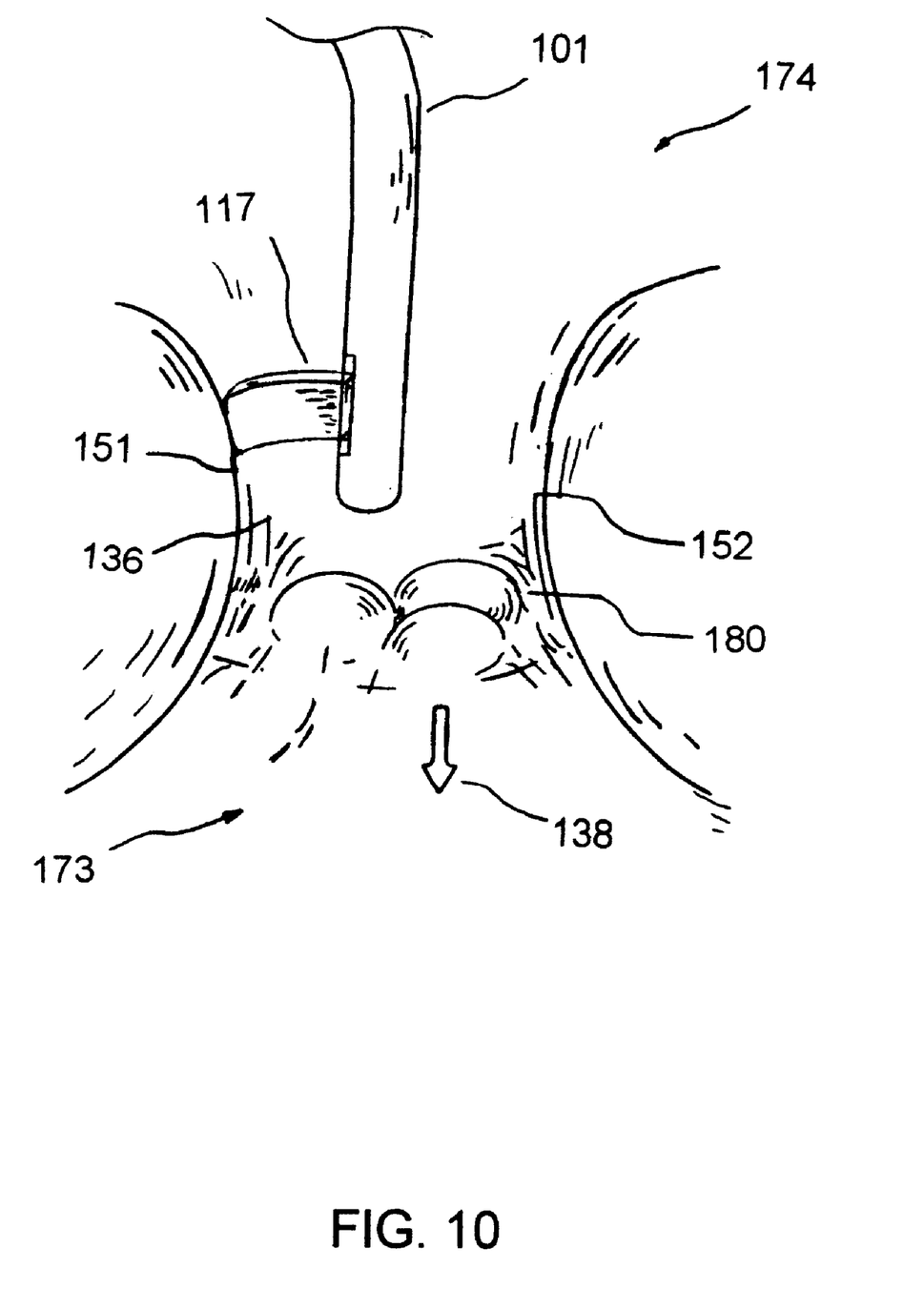
FIG. 10 is a close-up simulated perspective view of the valvular annulus of FIG. 9 being treated by the medical device of the present invention.

FIG. 10 shows a close-up simulated view of the catheter system of the present invention in contact with the tissue of an annular organ structure 152. For illustration purposes, a catheter 101 having an extendible electrode 117 at a distal section of the catheter is inserted into the right atrium 174. The bloodstream (as shown by an arrow 138) flows from the right atrium 174 through a tricuspid valve 180 to the right ventricle 173. The extendible electrode 117 contacts the inner wall 151 of an annular organ structure 152. High frequency energy may be applied to the tissue of the annular organ structure through the contacting electrode 117 of the present invention.

During procedures, the flexible catheter is inserted into the body of a patient through a natural opening or a surgical hole. For one embodiment, a method for operating a catheter system for treating a valvular annulus, the method comprises the steps of (a) percutaneously introducing the catheter system through a blood vessel to a valvular annulus, the catheter system comprising a flexible elongate tubular element having a distal section, a distal end, a proximal end, and at least one lumen extending therebetween, wherein an opening is located at one side of the distal section; an inner tubing located within the lumen of the elongate tubular element, the inner tubing having a distal section, a distal end, a proximal end, and a lumen extending therebetween, wherein a deployable electrode is located at the distal section of the inner tubing, the deployable electrode comprising a pre-shaped extendible electrode that stays within the lumen of the elongate tubular element under a non-deployed state and extends out of the elongate tubular element through the opening during a deployment state; a handle attachably secured at the proximal end of the tubular element, the handle having a cavity; and an external RF energy generator having a conducting wire, wherein the energy is supplied to the deployable electrode through the conducting wire; (b) positioning the tip of the catheter system about an entrance region of the valvular annulus; (c) deploying the extendible electrode out of the opening of the elongate tubular element of the catheter system; and (d) applying RF energy to the extendible electrode of the catheter system to effect heat treatment of the valvular annulus.

From the foregoing description, it should now be appreciated that a medical ablation device system, including a catheter-like device, for the endometrosis, cysts, gingivae, polyps, prostate, tumors, valvular annulus, or cellular tissues treatment, comprising a suitable energy source and a rotational sweeping massage therapy, with an optional fluid irrigation capability has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for treating the endometrosis of a patient with a medical ablation device system, the device system comprising an elongate tubular element having a distal section, a distal end, a proximal end, and at least one lumen extending therebetween, wherein an opening is located at one side of the distal section; an inner tubing located within the lumen of the elongate tubular element, the inner tubing having a distal section, a distal end, a proximal end, and a lumen extending therebetween, wherein a deployable electrode is located at the distal section of the inner tubing, the deployable electrode comprising a pre-shaped extendible electrode that stays within the lumen of the elongate tubular element under a non-deployed state and extends out of the elongate tubular element through the opening during a deployment state; a handle attachably secured at the proximal end of the tubular element, the handle having a cavity; and an external RF energy generator having a conducting wire, wherein the energy is supplied to the deployable electrode through the conducting wire;

the method comprising the steps of:
   (a) inserting the medical ablation device system into the abdominal cavity of a patient using a standard laparoscopic technique;
   (b) positioning the tip of the device system upon the wall of the abdominal cavity where an endometrosis prevails;
   (c) deploying the extendible electrode out of the opening of the elongate tubular element of the device system; and
   (d) applying RF energy to the extendible electrode of the device system to effect heat treatment of the endometrosis.

2. The method for treating the endometrosis of a patient of claim 1 further comprising rotating the distal section of the elongate tubular element, wherein the means for generating rotational motion for the distal section of the elongate tubular element comprising a motor mounted in the cavity of the handle of the device system, which has a rotatable motor shaft, an elongate connecting shaft having a first end to which the proximal end of the elongate tubular element is connected, and a second end connected to the motor, so that when the motor shaft rotates, the elongate tubular element also rotates.

3. The method for treating the endometrosis of a patient as in claim 1, the device system further comprising a temperature sensor, wherein the temperature sensor is located at the distal section of the medical ablation device system.

4. The method for treating the endometrosis of a patient as in claim 3, the device system further comprising a temperature controller, wherein the temperature measured from the temperature sensor is relayed to the temperature controller adapted to effect the energy supply of the RF energy generator.

5. The method for treating the endometrosis of a patient of claim 1, wherein the electrode of the device system is selected from the group consisting of a curved plate, a plurality of curved wires, a curved plate with studded surface, a plurality of coils, a curved wire with a needle end, and a meshed plate.

6. The method for treating the endometrosis of a patient as in claim 1, the medical ablation device system further comprising a hollow passage within the lumen of the inner tubing, a fluid inlet port at the proximal end portion of the inner tubing, wherein the hollow passage is to provide fluid communication and flow of fluid originating from the fluid inlet port through the opening to portions of the exterior surface of the extendible electrode which direct the fluid flow from inside the inner tubing over the exterior surface to provide a fluid protective layer surrounding the extendible electrode to minimize temperature elevation of the extendible electrode in contact with biological tissues.

7. The method for treating the endometrosis of a patient of claim 6, wherein the fluid is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, antiinflammatory agents, antibiotics, and their mixtures.

8. A method for operating a catheter system for treating a valvular annulus of a patient, the method comprising the steps of:
   (a) percutaneously introducing the catheter system through a blood vessel to the valvular annulus, the catheter system comprising a flexible elongate tubular element having a distal section, a distal end, a proximal end, and at least one lumen extending therebetween, wherein an opening is located at one side of the distal section; an inner tubing located within the lumen of the elongate tubular element, the inner tubing having a distal section, a distal end, a proximal end, and a lumen extending therebetween, wherein a deployable electrode is located at the distal section of the inner tubing, the deployable electrode comprising a pre-shaped extendible electrode that stays within the lumen of the elongate tubular element under a non-deployed state and extends out of the elongate tubular element through the opening during a deployment state; a handle attachably secured at the proximal end of the tubular element, the handle having a cavity; and an external RF energy generator having a conducting wire, wherein the energy is supplied to the deployable electrode through the conducting wire;
   (b) positioning the tip of the catheter system about an entrance region of the valvular annulus;
   (c) deploying the extendible electrode out of the opening of the elongate tubular element of the catheter system;

(d) applying RF energy to the extendible electrode of the catheter system to effect heat treatment of the valvular annulus; and (e) rotating the distal section of the elongate tubular element.

9. The method for operating a catheter system for treating a valvular annulus of a patient of claim 8, wherein means for generating rotational motion for the distal section of the elongate tubular element comprising a motor mounted in the cavity of the handle of the catheter system, which has a rotatable motor shaft, an elongate connecting shaft having a first end to which the proximal end of the elongate tubular element is connected, and a second end connected to the motor, so that when the motor shaft rotates, the elongate tubular element also rotates.

10. The method for operating a catheter system for treating a valvular annulus of a patient of claim 8, wherein the valvular annulus is selected from the group consisting of the valvular annulus of a mitral valve, a tricuspid valve, a pulmonary valve, an aortic valve, and a venous valve.

11. A method for treating the endometrosis of a patient with a medical ablation device system, the device system comprising an elongate tubular element having a distal section, a distal end, a proximal end, and at least one lumen extending therebetween, wherein an opening is located at one side of the distal section; an inner tubing located within the lumen of the elongate tubular element, the inner tubing having a distal section, a distal end, a proximal end, and a lumen extending therebetween, wherein a deployable electrode is located at the distal section of the inner tubing, the deployable electrode comprising a pre-shaped extendible electrode that stays within the lumen of the elongate tubular element under a non-deployed state and extends out of the elongate tubular element through the opening during a deployment state; a handle attachably secured at the proximal end of the tubular element, the handle having a cavity; and an external RF energy generator having a conducting wire, wherein the energy is supplied to the deployable electrode through the conducting wire;

the method comprising the steps of:

(a) inserting the medical ablation device system into the uterus of a patient using a standard inserting technique;

(b) positioning the tip of the device system upon the wall of the uterus where an endometrosis prevails;

(c) deploying the extendible electrode out of the opening of the elongate tubular element of the device system; and (d) applying RF energy to the extendible electrode of the device system to effect heat treatment of the endometrosis.

12. The method for treating the endometrosis of a patient as in claim 11, the device system further comprising a temperature sensor, wherein the temperature sensor is located at the distal section of the medical ablation device system.

13. The method for treating the endometrosis of a patient as in claim 11, the device system further comprising a temperature controller, wherein the temperature measured from the temperature sensor is relayed to the temperature controller adapted to effect the energy supply of the RF energy generator.

14. The method for treating the endometrosis of a patient of claim 11, wherein the electrode of the device system is selected from the group consisting of a curved plate, a plurality of curved wires, a curved plate with studded surface, a plurality of coils, a curved wire with a needle end, and a meshed plate.

15. The method for treating the endometrosis of a patient as in claim 14, the device system further comprising a temperature sensor, wherein the temperature sensor is located at the distal section of the medical ablation device system.

16. The method for treating the endometrosis of a patient as in claim 14, the device system further comprising a temperature controller, wherein the temperature measured from the temperature sensor is relayed to the temperature controller adapted to effect the energy supply of the RF energy generator.

17. The method for treating the endometrosis of a patient of claim 14, wherein the electrode of the device system is selected from the group consisting of a curved plate, a plurality of curved wires, a curved plate with studded surface, a plurality of coils, a curved wire with a needle end, and a meshed plate.

* * * * *